(12) United States Patent
Quinn et al.

(10) Patent No.: US 11,266,573 B2
(45) Date of Patent: Mar. 8, 2022

(54) SYSTEM FOR DOSING AND DISPENSING MEDICATION

(71) Applicants: Michael Vincent Quinn, East Hanover, NJ (US); Alexander Gorshkov, Somerville, NJ (US); Richard Cronenberg, Mahwah, NJ (US); Tor Alden, Basking Ridge, NJ (US); Robert Boyer, Boonton, NJ (US)

(72) Inventors: Michael Vincent Quinn, East Hanover, NJ (US); Alexander Gorshkov, Somerville, NJ (US); Richard Cronenberg, Mahwah, NJ (US); Tor Alden, Basking Ridge, NJ (US); Robert Boyer, Boonton, NJ (US)

(73) Assignee: SYMPFINY LLC, Morristown, NJ (US)

( * ) Notice: Subject to any disclaimer, the term of this patent is extended or adjusted under 35 U.S.C. 154(b) by 117 days.

(21) Appl. No.: 15/968,515

(22) Filed: May 1, 2018

(65) Prior Publication Data
US 2018/0311110 A1    Nov. 1, 2018

Related U.S. Application Data

(60) Provisional application No. 62/492,868, filed on May 1, 2017.

(51) Int. Cl.
*A61J 7/00*     (2006.01)
*A61J 1/00*     (2006.01)
(Continued)

(52) U.S. Cl.
CPC ............... *A61J 7/0053* (2013.01); *A61J 1/00* (2013.01); *A61J 7/0076* (2013.01);
(Continued)

(58) Field of Classification Search
CPC ...... A61J 1/1406; A61J 1/2037; A61J 1/1475; A61J 1/2044; A61J 1/2048; A61J 1/2096;
(Continued)

(56) References Cited

U.S. PATENT DOCUMENTS 5,702,019 A * 12/1997 Grimard ............... A61J 1/2096
141/24
2001/0020147 A1* 9/2001 Staniforth ......... A61M 15/0066
604/58

(Continued)

FOREIGN PATENT DOCUMENTS

EP      2022379 A1    2/2009
GB      2187388 A     9/1987
(Continued)

OTHER PUBLICATIONS

WIPO, International Bureau, International Preliminary Report on Patentability, for PCT/US2018/030544, PCT counterpart of US application, dated Nov. 14, 2019.

(Continued)

*Primary Examiner* — Amber R Stiles
*Assistant Examiner* — Avery Smale
(74) *Attorney, Agent, or Firm* — Benjamin Appelbaum (57) ABSTRACT

A system for medication delivery comprises a package containing a medication and a dosing device for delivering a dose of the medication, formulated as a multiparticulate, microspheres, a powder or a liquid. The package comprises a bottle, a bottle insert that covers a bottle opening and includes a dispense nozzle. The dispense nozzle is sealed using a valve that opens when the dosing device is engaged with the bottle. A closure covers the bottle insert and closes the bottle. The dosing device, similar to an oral syringe, comprises a barrel with a valve at a distal end of the barrel, a plunger and a dose control clip for attachment to the (Continued)

plunger. After the dosing device is connected to, the valve of the dispense nozzle, withdrawal of the plunger causes the dosing device to receive the dose of the medication, a user pushes the plunger which pushes the medication through the valve of the barrel and into a patient's mouth.

5 Claims, 9 Drawing Sheets

(51) Int. Cl.
  *A61M 5/315* (2006.01)
  *B65D 83/06* (2006.01)
  *A61M 39/26* (2006.01)
  *A61M 5/50* (2006.01)

(52) U.S. Cl.
  CPC ...... *A61M 5/3156* (2013.01); *A61M 5/31501* (2013.01); *A61M 5/31563* (2013.01); *A61M 39/26* (2013.01); *B65D 83/06* (2013.01); *A61J 2200/76* (2013.01); *A61M 2005/3154* (2013.01); *A61M 2005/31508* (2013.01); *A61M 2005/5033* (2013.01); *A61M 2039/267* (2013.01)

(58) Field of Classification Search
  CPC .......... A61J 7/0053; A61J 1/00; A61J 7/0076; A61M 2005/31508; A61M 39/26; A61M 5/3134; A61M 2005/3103; A61M 2005/3106; A61M 5/31563; A61M 5/31501; A61M 5/3156; A61M 2039/267; A61M 2005/5033; A61M 2005/3154; B65D 83/06
  See application file for complete search history.

(56) References Cited

U.S. PATENT DOCUMENTS

| | | | |
|---|---|---|---|
| 2004/0143224 A1* | 7/2004 | Field | A61M 5/31511 604/195 |
| 2007/0000953 A1 | 1/2007 | Ranney | |
| 2007/0078119 A1* | 4/2007 | Purro | A61K 9/0019 514/185 |
| 2007/0187433 A1 | 8/2007 | Webster | |
| 2010/0241088 A1 | 9/2010 | Ranalletta | |
| 2013/0180618 A1* | 7/2013 | Py | A61J 1/1406 141/2 |
| 2014/0336591 A1* | 11/2014 | Skaper | A61M 5/31555 604/208 |
| 2014/0336951 A1 | 11/2014 | Raumedic | |

FOREIGN PATENT DOCUMENTS

WO      2006 124756 A2      11/2006
WO      2009 061480 A1      5/2009

OTHER PUBLICATIONS

WIPO International Searching Authority, International Search Report for PCT/US2018/030544, PCT counterpart of US application, dated Sep. 12, 2018.
WIPO, International Searching Authority, Written Opinion of the International Searching Authority, for PCT/US2018/030544, PCT counterpart of US application, dated Sep. 12, 2018.
Lengyel, M. et al. Multiparticules, Microspheres, and Microcapsules For Advanced Drug Delivery, Scientia Pharmaceutica, 2019 87:20 doi:10.3390/scipharm 87030020.
13th Annual Conference European Paediatric Formulation Initiative EUPFI 2020-Virtual, 2021 downloaded from the Internet on Apr. 2, 2021, from http://eupfi.org/upcoming-conference/13th-eupfi-conference-virtual-.
Bartlett, J.A. et al. Pediatric Formulation Development—Industry Perspective on Palatability Challenges and Opportunities, 2016, Presentation at CERSI Workshop in collaboration with EuPFI & IQ Consortium, Hyattsville, MD; downloaded from the Internet on Feb. 8, 2021, from https://www.pharmacy.umaryland.edu/media/SOP/wwwpharmacyumarylandedu/centers/cerseievents/pedsformulation/bartlett-presentation-notes.pdf.
Pfizer Corp. Pfizer and The Institute of Pediatric Innovation Issue Open Innovation Challenge, May 24, 2016, downloaded from the Internet on Mar. 22, 2021, from https://pfizer.com/news/featured/featured_stories_detail/pfi . . . .
Narsalay, R et al. Open Innovation at Pfizer, Accenture Co., 2017 downloaded from the Internet on Mar. 22, 2021, from www.ideaconnection.com.pdf.pfizer.
PRWEB, Pediatric Open Innovation Challenge Grantees Awarded $50,000 by the Institute for Pediatric Innovation and Pfizer, Dec. 12, 2016, downloaded from the Internet on Mar. 22, 2021, from www.prweb.com.releases.2016/12.prweb13889068.

* cited by examiner

SYSTEM FOR DOSING AND DISPENSING MEDICATION

CROSS-REFERENCES TO RELATED APPLICATIONS

This application claims the benefit of United States provisional application for patent Ser. No. 62/492,868, filed on 1 May 2017, by the present inventors, and whose content is incorporated by reference herein in its entirety.

STATEMENT REGARDING FEDERALLY SPONSORED RESEARCH OR DEVELOPMENT

Not Applicable.

FIELD OF THE INVENTION

Embodiments of the present invention relate to syringes and drug bottles, more specifically, to a system and method for measuring and dispensing drugs to a patient. Drug formulations can include drugs formulated as multiparticulate, microspheres or powders for oral administration, and liquid drugs for administration orally or other administration routes.

BACKGROUND OF THE INVENTION

The vast majority of pediatric formulations today are oral solutions or suspensions. Liquid formulations are commonly used for the pediatric population for their ease of administration and ease of modifying the dose volume, but are limited by their need for large dosing volumes, bad taste that requires taste masking with sweeteners, and often the requirement for refrigeration during storage and transportation (cold chain storage and transportation). Solid oral doses have better dosing volumes, but can be difficult for children to swallow, and dose volumes are not easily changed by the user.

Children in low resource countries often do not receive the correct dose of medicine because pediatric formulations either are not available or existing formulations are not properly dosed. Powder that can be reconstituted to a liquid solves the cold chain storage and transportation issue but requires potable water which might not be readily available in low-resource settings.

Children with taste sensitivities or difficulty swallowing can have significant issues taking a precise dose of liquid oral medications. The taste can cause vomiting, spitting or outright refusal to swallow the medicine. Likewise, adults with difficulty swallowing pills and tablets could also benefit from an easier to swallow form of medication.

The Multi-Particulate (MP) formulation brings together the advantages of both liquid and solid formulations—high dose flexibility and ease of administration—to facilitate the effective and safe administration of drugs for children and adults. MP drugs are microspheres of dry drug that can contain a coating that masks the flavor of the drug and can be designed to remain intact in water or saliva and only dissolve in mild acid, such as in a patient's stomach.

While MP drugs offer a solution to the difficulties of liquid oral medications and solid pills, they offer unique challenges to measuring a precise dose and administering that dose. MP drugs are shaped like tiny spheres, generally ranging from about 100 to about 400 microns in diameter. They have no surface tension to each other and so they flow more easily than water, but when put under compression they can lock against each other and not move at all. MP drugs are also sensitive to moisture and can clump if they get too moist.

Current solutions for dosing and dispensing MP and powdered drugs include the following: Unit doses in foil lined packets, Unit doses in break-open capsules and Unit doses in filter straws. In the case of the packets and capsules, the MP needs to be poured into the patient's mouth or onto a secondary dispensing device, such as a spoon. Dispensing using gravity into a mouth requires the patient to tilt his or her head back. It is also difficult to guide the MP into a location in the mouth that is acceptable and will not cause the patient to spit or cough it out, such as the inside of the cheek. Pouring it into the mouth usually results with the MP resting on the tongue instead. Dispensing onto a spoon is feasible for children who are old enough to use a spoon, or who have a care-giver who can handle a spoon; this still introduces a high probability of some drug spilling from the spoon, reducing the effective dose to the patient.

The other difficulty using packets or capsules is when different doses are needed than what is contained in a single capsule or packet. To achieve variable dose levels a care giver needs to combine capsules of identical or different dosages. This introduces chances of errors and spilling.

Filter straws are another method of dispensing MP drugs. They are a single-use disposable drinking straw with a filter at one end. The MP is contained within the straw and a child drinks through the straw, pulling the MP up with the diluent, generally water, and into the mouth. This avoids the spilling potential but it is only suitable for children old enough to use drinking straws. It is a fixed dose system and uses a disposable device for each dose that is more expensive than a capsule or packet.

What is desirable is a system that can be used to measure a dose of MP drug and then dispense it to even the youngest pediatric patients with high probability of an accurately delivered dose. The system should be useable by parents and/or other care givers with little or no training. The system should be suitable for use in most environments, including low resource environments. The system should also be suitable for use by geriatric patients who have swallowing problems or related difficulties, as well as people of other ages who have similar medical problems, such as, for example only, the result of an accident.

Traditional liquid medications that are drawn into a syringe are done so in two common ways. One is with a needle at the end of the syringe which punctures a septum or dips into a bottle. The other, commonly used for liquid oral medication, is to place the end of the syringe, typically a luer-style nozzle, into a bottle such that the nozzle is inserted into a matching hole in the top of the bottle. The system is inverted with the syringe below the bottle and then the plunger is drawn back to align with a printed dose marking, pulling the liquid into the syringe. The syringe is then separated from the bottle. In these systems the liquid is prevented from spilling out of the syringe and bottle only by means of surface tension of the liquid and the size of the openings, along with the user keeping the opening upright; however, none of these methods are absolute and leaking often occurs. Furthermore, the dose volume is selected visually by the user. What is desirable is a means to prevent leaking from the bottle and the syringe, especially with expensive drugs or those which skin contact is undesirable. What is also desirable is a means to set a dose that is more accurate and repeatable than by visual alignment of the plunger rod to a printed marking on the syringe barrel.

BRIEF SUMMARY OF THE INVENTION

Embodiments of the present invention include a system for medication (drug) delivery that comprises two separate assemblies: a Package that will contain a drug and a Dosing mechanism (or device) for delivering a dose of the medication. The system is suited for drugs formulated as multiparticulate, microspheres, or powder, and could also be used for liquid drugs. For purposes of the present specification, the term drug will be referred to as MP drug and is intended to include multiparticulates, microspheres and powder.

The Package is a container, such as a bottle, that could contain a full course of therapy of an MP drug. A full course of therapy could range from as few as 1-2 days to a couple of months supply, the maximum quantity often limited by health insurance restrictions. This Package can either be filled by a pharmaceutical company or filled at a local pharmacy. The Package comprises a bottle, a bottle insert that covers the opening of the bottle and which contains a dispense nozzle. The dispense nozzle is sealed using a valve. The valve can be a split septum rubber valve. The valve will only open when the Dosing device is engaged with the bottle during extraction of a dose. The bottle assembly is closed with a closure, such as a child resistant cap (commonly a push-and-turn screw cap), that covers the bottle insert. When necessary, a non-child resistant cap can be utilized in place of the child-resistant cap.

The Dosing device is similar in form to an oral syringe and comprises a barrel with a valve at its distal end, a plunger which seals against the inside of the barrel, and a dose control mechanism (clip) on the outside diameter of the plunger. The plunger contains one or more grooves around its circumference into which the dose control clip can be placed. The placement of the dose control clip into one of the grooves creates a larger diameter ring around the plunger that will be bigger than an internal ring at the rear of the barrel. When the plunger is pulled rearward the dose control clip will create a positive stop against the barrel and provide a precise location of the plunger rod inside the barrel and in turn a precise volume into which MP drug can flow.

When dispensing an MP drug from the Dosing Device ("Device"), the user pushes against the proximal end of the plunger. The force of the plunger pushes the MP drug, which in turn pushes open the valve at the distal end of the Device. The MP drug is pushed through the valve and into the patient's mouth. When force is removed from the plunger the valve closes, preventing spills of any MP drug remaining in the Device.

A method of measuring and dispensing a Multiparticulate drug (MP) to a patient comprises several steps. The person performing these steps may be a caregiver to a patient, the patient themself, or another person. The steps include uncapping a Package containing the MP drug, then connecting the Device to the fill nozzle of the uncapped package. Connecting the Device to the fill nozzle automatically opens both the bottle valve and the barrel valve, creating a flow path between the bottle and the inside of the Device barrel. Another step is inverting the bottle and allowing the MP drug to flow by gravity into the barrel. The amount of MP drug that enters into the barrel is determined by pulling back on the plunger to a specified position. The specified position is selected by placing a clip onto the plunger rod, or by visually lining up the plunger rod end to printed dose markings on the Device barrel.

After the barrel has been filled with the specified quantity of the MP drug, the method further includes the step of removing the Device from the bottle fill nozzle.

The valves in both the Package and Device automatically close and prevent the MP drug from spilling out of the Package or Device. The method further includes the step of placing the Device distal end within a patient's mouth or a secondary device. Depressing the Device plunger from the proximal end toward the distal end causes the MP drug to be dispensed from the Device. The device can also be used to deliver MP drug indirectly to a patient by dispensing the measured amount of drug to a secondary device such as a spoon, another container, or onto and/or mixed in with food or into a beverage.

Another embodiment of the present invention includes a dose metering chamber within the bottle. This embodiment gives the user the ability to meter a dose using the bottle and then dispense the dose into a container, syringe, or into a patient's mouth, food, etc. . . . without the need to use a syringe with precise dose control. To select a dose volume, the user rotates the proximal end of the bottle relative to the distal end until the desired dose will be displayed in the dosing window on the side of the bottle. The user then holds the bottle with the dispense port facing downward and positioned over the container or food that the multiparticulate is to be dispensed into. Once positioned the user depresses the dispense button on the side of the bottle and the MP drug will flow out of the bottle in the precise dose selected.

The bottle includes a primary chamber for storing a quantity of the MP drug and an intermediate chamber that is sized to contain a single dose volume. The intermediate chamber size can be changed by rotating the insert. The chamber is a cylinder containing two dividing walls radiating out from the center. Rotating the insert rotates one of these dividing walls to create a semicircular volume within the cylinder. The more degrees it rotates through, the smaller the trapped volume in the cylinder becomes. Alternately, the chamber size could be adjusted by means of a screw mechanism that would translate the rotation of the insert to a linear movement of the chamber floor.

The dispense button controls movement of the MP drug from the primary chamber to the intermediate chamber. The dispense button can also control the movement of the MP drug from the intermediate chamber into the dispense port and ultimately out of the bottle. The dispense button is linked to two sliding gates: one between the primary chamber and the intermediate chamber (gate 1) and the other between the intermediate chamber and the dispense port (gate 2). While the dispense button is in its non-depressed state, gate 1 is open, allowing the MP drug to flow from the primary chamber into the intermediate chamber and gate 2 is closed, preventing the MP drug from flowing out of the dispense port. When the dispense button is pressed gate 1 first closes the intermediate chamber from the primary chamber and gate 2 then opens the intermediate chamber to the dispense port.

BRIEF DESCRIPTION OF THE SEVERAL VIEWS OF THE DRAWING

FIG. 3c is an isometric view of the distal end of the syringe shown in FIG. 3a.

FIG. 6a is a side view of the Syringe assembly as an MP drug is being dispensed to a patient.

FIG. 6b is a cross sectional view of the syringe assembly shown in FIG. 6a.

FIG. 7a is a side view of the Syringe assembly at the end of the dispensing stroke.

FIG. 7b is a cross sectional view of the syringe assembly shown in FIG. 7a.

DETAILED DESCRIPTION OF THE INVENTION

Embodiments of the present invention include a system for drug delivery, and more particularly to formulations such as multiparticulate, microsphere, or powdered drug ("MP drug") delivery that comprises two separate assemblies: a Package for storage of the MP drug and a Dosing device for delivering a dose of the MP drug.

Conventional medications for children often take the form of a liquid that is taken orally. These liquid oral medications are often measured and dispensed by means of a spoon, a cup or a syringe into the patient's mouth. These liquid oral medications often require taste masking in the form of sweeteners and flavorings to help make them palatable since the actual medications often taste very bad, especially to children. The properties of some medications are such that taste masking is ineffective. Taste is subjective and region specific, so manufacturers often have to develop many different flavors for each drug. Furthermore, some liquid medicines have to be kept cold for storage during transport and that makes them more expensive and harder to supply in regions without ready access to refrigeration. The multiparticulate drug formulation is an alternative to liquid oral medication; many MP drugs can be tasteless and do not require refrigeration.

MP drugs have their own physical properties that make traditional oral syringes unsuitable for use. The MP drug is formulated as a plurality of micro spheres which do not stick together and allow air to pass through them. This makes drawing them into a syringe using suction created by the plunger rod difficult. It also means they will pour out of very small openings such as the tip of a syringe even if the syringe plunger is not being advanced. MP drugs require a reliable and intuitive way to measure a dose and deliver it to the patient.

Figure 1A:
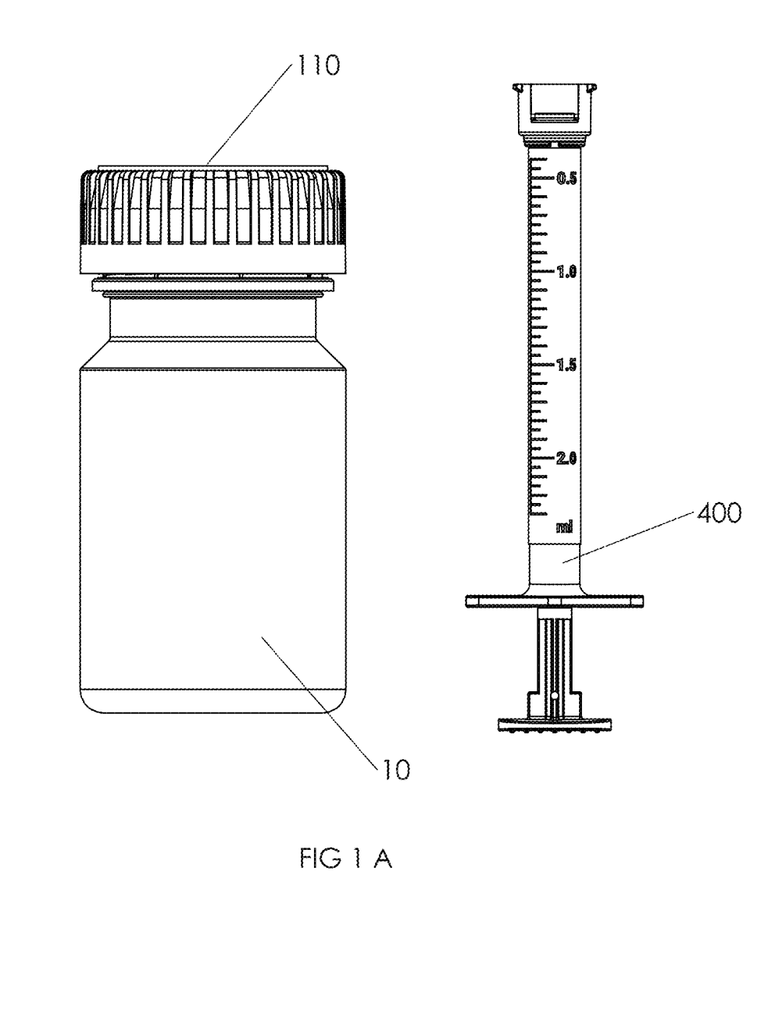
FIG. 1*a* is a side view of the system including bottle with cap suitable for storing an MP drug and a syringe (dosing device).
Figure 1B:
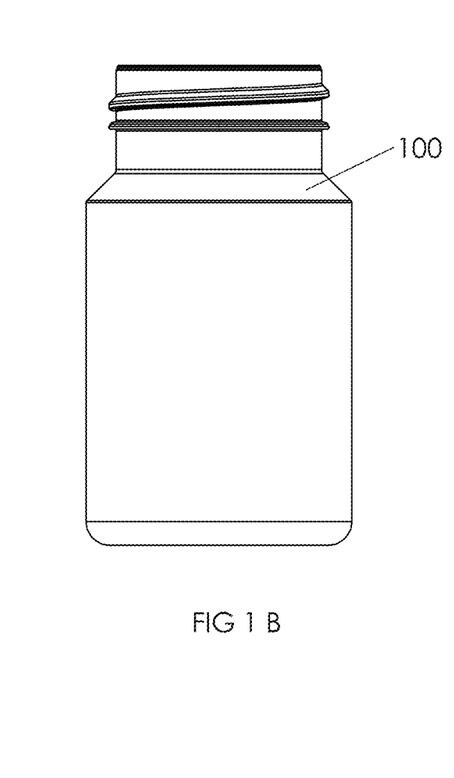
FIG. 1*b* is a side view of the bottle with the cap removed.
Figure 2:
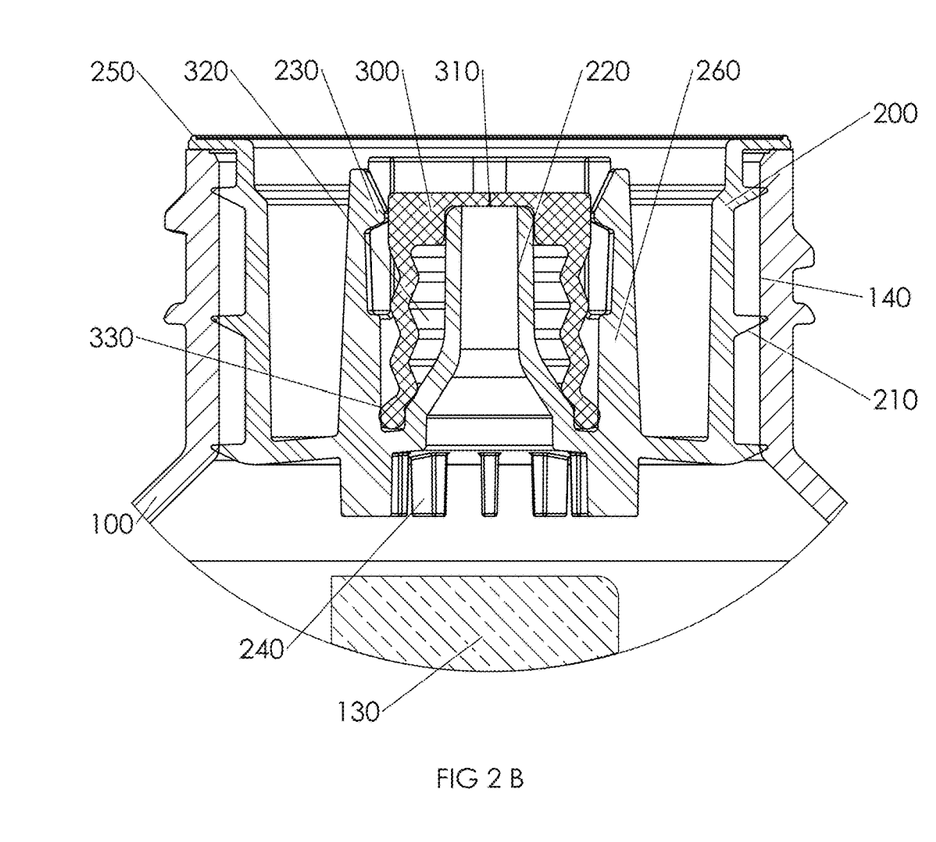
FIG. 2*a* is a cross-sectional view of the bottle shown in FIG. 1*b*.
FIG. 2*b* is a close-up view of the bottle insert shown in FIG. 2*a*.
Figures 3A, 3B:
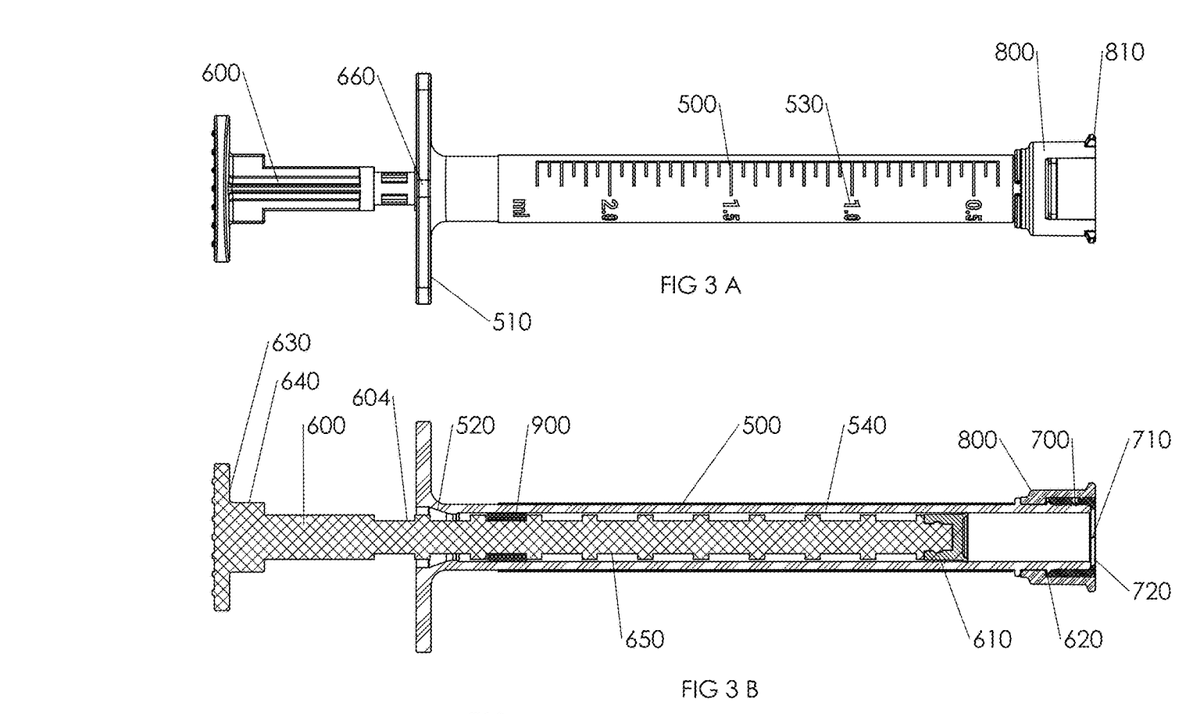
FIG. 3*a* is a side view of the syringe assembly for delivering MP drug to a patient.
FIG. 3*b* is a cross-sectional view of the syringe assembly shown in FIG. 3*a*.
Figure 3C:
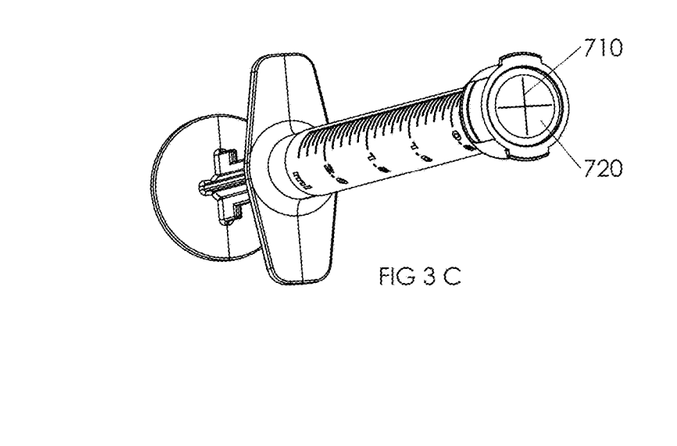

A device embodiment of the present invention includes the package 10 (FIG. 1a) which contains a specified quantity of the drug and a dosing device 400 in the form of a syringe (FIG. 3a). The package comprises a bottle 100, a bottle cap 110 used to seal and protect the contents of the package. The bottle cap 110 may be of a child-resistant design, or it may be a non-child-resistant cap, or low resistant cap such as for arthritic persons. The bottle 100 includes an insert 200 (FIG. 2a) that covers the opening of the bottle 100 when the cap is off, and a valve body 300 (also referred to as a split septum valve). The bottle insert seals against the bottle inner wall 140 by an interference fit of the sealing ribs 210 (FIG. 2b). The bottle cap 110 seals against the bottle insert 200 by contact with the insert's cap seal ring 250. The bottle valve 300 seals against the bottle insert 200 by interference fit of the bottle valve seal ring 330. The seals 210, 250 and 330 ensure that the drug can be protected from moisture in the air which might cause the drug to clump and not be able to flow out of the bottle when needed. The bottle 100 has room for a desiccant 130, contained in a capsule or bag, to be packaged and shipped with the drug. The desiccant maintains a humidity level in the bottle 100 that is optimal for the MP drug 120. The back of the bottle insert 200 includes one or more anti-clog ribs 240 that prevent the desiccant 130 from clogging the dispense nozzle 220 (FIG. 2b). The dispense nozzle 220 is where the MP drug will flow through once a dosing device 400 (syringe) is connected to the bottle. The nozzle 220 is normally closed by means of the valve body 300. This valve body 300 includes a slit 310 through which the dispense nozzle 220 can be inserted, a spring bellows 320 for biasing the valve into a closed position, and a seal ring 250 for securing the valve to the bottle insert 200.

Figure 4:
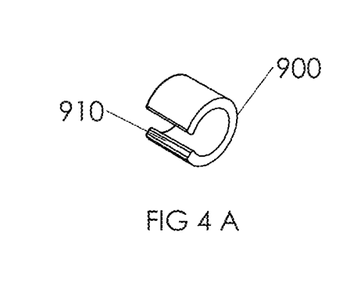
FIG. 4a is a perspective view of the Dose control clip removed from the plunger rod.
FIG. 4b is a side view of the plunger rod assembly removed from the syringe.

The dosing device (syringe) 400 (FIG. 3a) comprises a barrel 500 with a valve 700 at its distal end (FIG. 3b), a plunger 600 having a plunger head 610 which seals against the inside 540 of the barrel by means of a sealing edge 620, and dose control clip 900 for mounting on the outside diameter of the plunger (FIG. 3b). Plunger 600 comprises a plunger rod 604, a forward stroke stop component 640 and a plunger thumb press 630. The plunger rod 604 terminates at plunger head 610. A plurality of grooves 650 are positioned at specified intervals along the length of plunger rod 604, and FIG. 4B shows the dose markings 660 around plunger rod 604 into which the dose control clip 900 (FIG. 4A) can be placed. The dose control clip 900 is placed into one of the grooves 650 by snapping the clip slot 910 over one of the grooves 650. The placement of the dose control clip 900 into one of the grooves 650 creates a larger diameter ring around the plunger 600 that is bigger than the internal barrel retaining ring 520 at the proximal end of the barrel 500 (FIG. 3B). When the plunger 600 is pulled rearward the dose control clip 900 creates a positive stop against the barrel retaining ring 520 and provides a precise location for the plunger head 610 inside the barrel 500 and in turn a precise volume into which the MP drug 120 can flow. At the distal end of the syringe 400 is the syringe valve 700 which covers the end of the barrel and a valve retaining ring 800 to hold the valve 700 in place and protect it from damage (FIGS. 3A and 3B). Both the plunger 600 and the dose control clip 900 are made of a flexible material, such that both the plunger 600, either with or without the dose control clip 900, can be withdrawn through the proximal end of the syringe, enabling the plunger 600, either with or without the dose control clip 900 attached, to be removed, for example, for cleaning.

Figure 5:
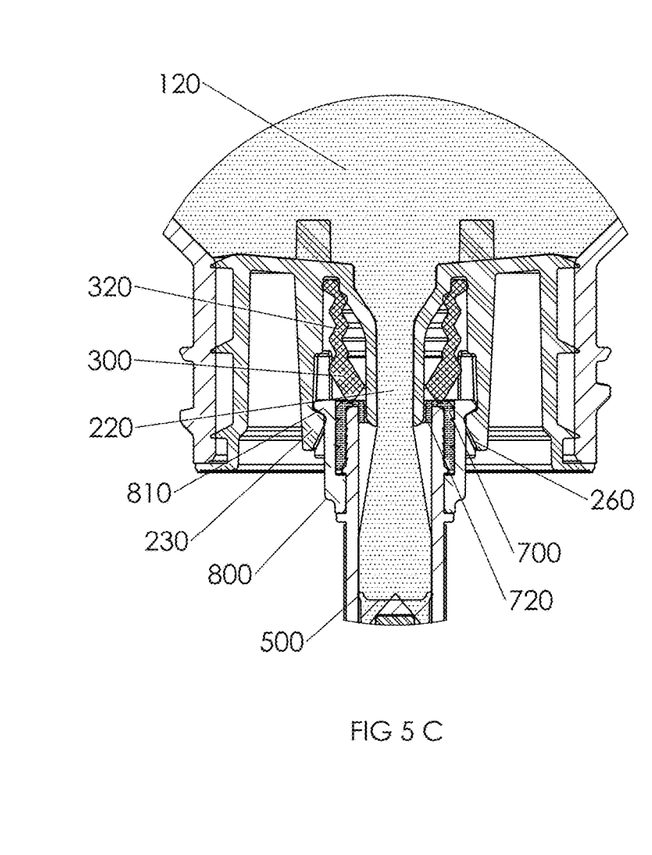
FIG. 5a is a side view of the Syringe inserted into the bottle during filling of the syringe.
FIG. 5b is a cross-sectional view of the Syringe and Bottle shown in FIG. 5a, taken along line A-A.
FIG. 5c is a close-up cross-sectional view of the Syringe and Bottle shown in FIG. 5b. with focus on the dispense nozzle and valves.

Referring to FIG. 5, the syringe 400 is filled for a single dose by connecting it to the package 10 and transferring a quantity of the MP drug 120 from the package 10 into the syringe 400 (FIG. 5a). This transfer is achieved by a series of steps. Depending upon the capacity of the syringe included with the device, and the dosage to be delivered, it may or may not be necessary to attach the dose control clip 900 to the plunger rod 604 before opening the bottle 100. A first step is removing the bottle cap 110. Using the syringe 400, the syringe valve retaining ring 800 is pressed into the bottle insert guide ring 260. Pressing them together causes the syringe valve retaining ring 800 to force the bottle valve 300 in a distal direction and around the dispense nozzle 220 (FIG. 5C). The dispense nozzle 220 pushes open the slit 310 of the bottle valve 300 and also the slits 710 in the syringe valve 700. The valve retaining ring 800 locks into place once the retaining ring lugs 810 snap into the bottle insert snap locks 230, providing tactile and audible feedback that the syringe is properly attached. The syringe plunger 600 is then pulled in a proximal direction until the dose control clip 900 comes in contact with the barrel retaining ring 520. The combined system of syringe 400 and package 10 are inverted such that the syringe 400 is below the package 10 (See FIGS. 5A and 5B, the bottom of the bottle 100 should be towards the ceiling.) and the MP drug 120 can then flow by means of gravity through the dispense nozzle 220 and into the syringe barrel 500. Once the barrel 500 is filled with the required amount of the drug the syringe 400 is disconnected from the bottle 100. The bottle and syringe valves close instantly upon disconnection. On the bottle side, the valve spring bellows 320 push the valve 300 to a closed position around the dispense nozzle 220. The syringe valve 700 closes simultaneously as the valve flaps 720 spring back to a neutral position.

Figure 6:
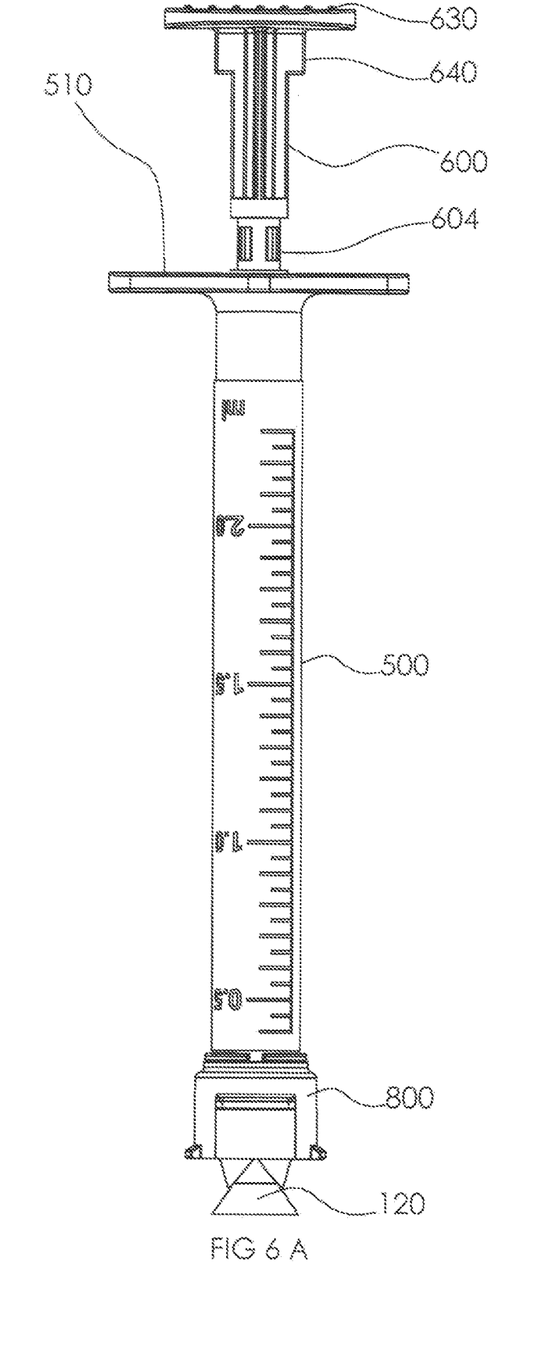
Figure 7:
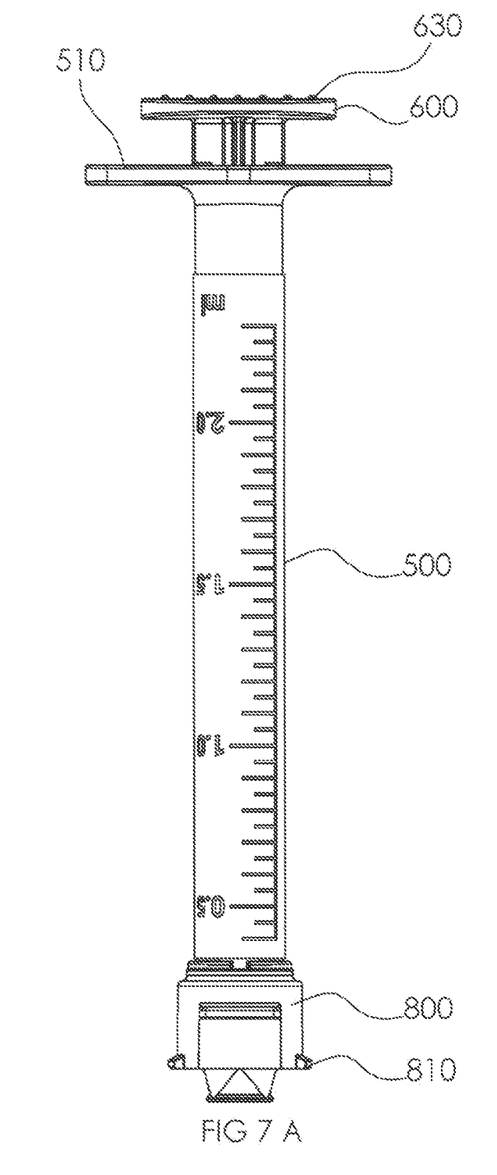

When dispensing the MP drug 120 from the Syringe 400 the user pushes against the proximal end of the plunger 600 using the plunger thumb press 630 (FIG. 6A). The force exerted on the plunger 600 pushes the MP drug 120, which in turn pushes open the valve 700 at the distal end of the Device. The valve 700 comprises flaps 720 created by slits 710 in the top of the valve (FIGS. 6B and 6C). The flaps 720 pivot outward by the force of the MP drug 120. If no force is being applied to the plunger 600, the flaps 720 remain in a neutral position across the top of the barrel 500 to prevent the MP drug 120 from spilling out of the syringe 400. To complete the dispensing of the MP drug the plunger 600 is pushed distally until the forward stroke stops 640 come into contact with the barrel flanges 510 (FIG. 7B), pushing the sealing edge 620 past the end of the barrel 500 and past the valve flaps 720, ensuring all the MP drug is expelled from the syringe. The inside of the valve flaps 720 become exposed, and any residual medication can be removed to prevent contamination, for example, by wiping the flaps 720 with a towel.

A method of measuring and dispensing a Multiparticulate drug (MP) to a patient comprises several steps. The person performing these steps may be a caregiver to a patient, the patient themself, or another person. The steps include uncapping a Package containing the MP drug, then connecting the Device to the fill nozzle of the uncapped package. Connecting the Device to the fill nozzle automatically opens both the bottle valve and the barrel valve, creating a flow path between the bottle and the inside of the Device barrel. Another step is inverting the bottle and allowing the MP drug to flow by gravity into the barrel. The amount of MP drug that enters into the barrel is determined by pulling back on the plunger to a specified position. The specified position is selected by placing a clip onto the plunger rod, or by visually lining up the plunger rod end to printed dose markings on the Device barrel.

Once the barrel is filled with the desired amount of MP drug, the Device is removed from the bottle fill nozzle. The valves in both the Package and Device automatically close and prevent MP from spilling out of the Package or Device. The Device distal end is then placed inside a patient's mouth. MP drug is dispensed from the Device by depressing the plunger from the proximal end toward the distal end. The device can also be used to deliver MP drug indirectly to a patient by dispensing the measured amount of drug to a secondary device such as spoon or other container, or onto food or into a beverage. For the purpose of this specification, when referring to the syringe, the proximal end is the end nearest where the barrel flanges are, and the distal end is the opposite end, where the syringe valve is located.

Another embodiment of the present invention includes a dose metering chamber within the bottle. This embodiment gives the user the ability to meter a dose using the bottle and then dispense the dose into a container, syringe, or into a patient's mouth, food, etc. . . . without the need to use a syringe with precise dose control. This alternate embodiment (FIG. 8) comprises a bottle 100 with a dispensing mechanism 270 (dose control bottle insert, or bottle insert) attached thereto.

Figure 8:
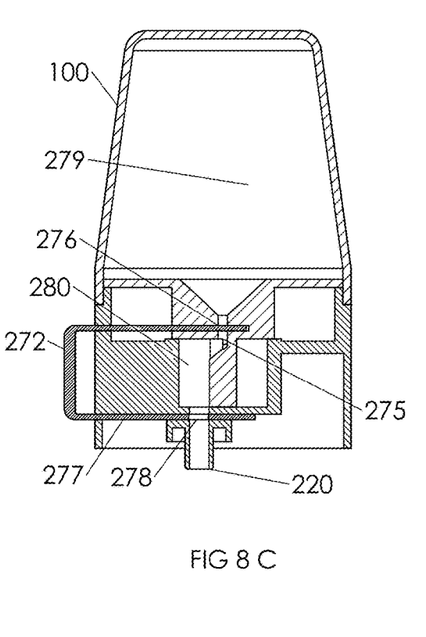
FIG. 8a is a side view of the bottle assembly having a dose control insert.
FIG. 8b is a cross section view of the bottle assembly having a dose control insert in the ready to dispense state.
FIG. 8c is a cross section view of the bottle assembly of FIG. 8a in the dispensing state.
FIG. 8d is a cross section view of the bottle showing the secondary dispense chamber.

To select a dose volume, the user would rotate the proximal end of the bottle relative to the distal end until the desired dose was displayed in the dosing window 274 on the side of the bottle. The user would then hold the bottle 100 with the dispense port 220 facing downward and positioned over the container or food that the multiparticulate is to be dispensed into. Once positioned the user depresses the dispense button 272 on the side of the bottle 100 and the MP drug (not shown) will flow out of the bottle in the precise dose selected.

Figure 9:
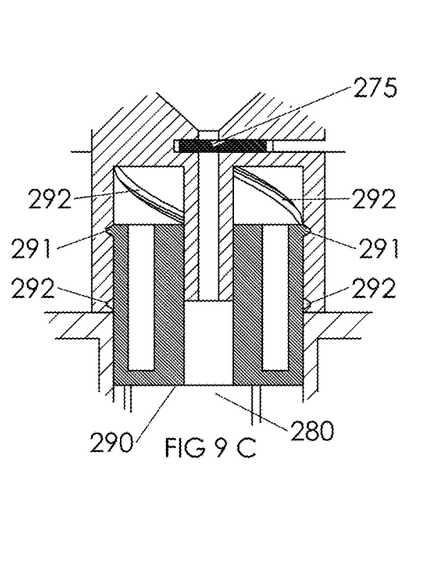
FIG. 9a is a cross section view of the bottle assembly having a dose control insert with screw mechanism in the ready to dispense state at minimum dose setting.
FIG. 9b is a cross section view of the bottle assembly having a dose control insert with screw mechanism in the dispensing state at minimum dose setting.
FIG. 9c is a detailed cross section view of the bottle assembly showing the screw mechanism interaction.

The bottle 100 includes a primary chamber 279 to contain the MP drug and an intermediate chamber 280 sized to contain a single dose volume. The size of the intermediate chamber can be changed by rotating the bottle insert 270. The intermediate chamber 280 is a cylinder containing two dividing walls 281, 282 radiating out from the center. Rotating the bottle insert 270 rotates one of these dividing walls 281, 282 to create a semicircular volume within the cylinder. The more degrees the bottle insert 270 rotates through, the smaller the trapped volume in the cylinder becomes. As shown in FIGS. 8B-8C, passage 275 connects the primary 279 and intermediate 280 chambers, and gates 1, 276 and gate 2, 277 cooperate in the dispensing of the drug as will be described further below. Alternately, the chamber 280's size could be adjusted by means of a screw mechanism that would translate the rotation of the insert 270 to a linear movement of the chamber roof 290 as shown in FIG. 9a-c. In said embodiment the Intermediate chamber roof 290 would have thread elements 291 that interact with threads 292 in the bottle. The chamber roof would be rotationally locked to the bottle insert 270 so that rotation of the bottle 100 vs the bottle insert 270 will result in translational movement of the chamber roof 290, thereby changing the volume contained in the chamber 280.

The dispense button 272 controls movement of the MP drug from the primary chamber to the intermediate chamber.

The dispense button 272 can also control the movement of the MP drug from the intermediate chamber 280 into the dispense nozzle 220 and ultimately out of the bottle. A spring (not shown) is positioned between the dispense button 272 and the intermediate chamber 280, the spring biasing the dispense button 272 into a non-depressed state. The dispense button 272 is linked to two sliding gates: one between the primary chamber and the intermediate chamber (gate 1, 276) and the other between the intermediate chamber and the dispense port (gate 2, 277). Gate 2 277 includes a hole 278 therethough (FIGS. 8B-8C). While the dispense button 272 is in its non-depressed state, gate 1 276 is open, allowing the MP drug to flow from the primary chamber 279 into the intermediate chamber 280 and gate 2 is closed, preventing the MP drug from flowing out of the dispense port (FIG. 8B). When the dispense button 272 is pressed gate 1 first closes the intermediate chamber 280 from the primary chamber 279 and gate 2 277 then positions hole 278 to open the intermediate chamber 280 to the dispense nozzle 220 (FIG. 8C).

Although embodiments of this invention have been described with a certain degree of particularity, it is to be understood that the present disclosure has been made only by the way of illustration, and that numerous changes in construction and arrangement of parts may be resorted to without departing from the spirit and scope of the invention. Table 1. Reference Numerals

NUMBER DESCRIPTION

10 Package
100 Bottle
110 Bottle cap
120 Multiparticulate Drug
130 Desiccant capsule
140 Bottle Inner Wall
200 Bottle Insert
210 Bottle Insert sealing rib
220 Bottle Insert dispense nozzle
230 Bottle Insert snap locks
240 Bottle Insert anti-clog ribs
250 Bottle Insert cap seal ring
260 Bottle insert guide ring
270 Dose Control Bottle Insert
272 Dispense button
275 Passage between primary and intermediate chambers
276 Gate 1
277 Gate 2
278 hole in Gate 2
279 Primary chamber
280 Intermediate chamber
281 Intermediate chamber dividing wall 1
282 Intermediate chamber dividing wall 2
290 Intermediate chamber roof
291 Interior chamber roof thread elements
292 Bottle thread elements
300 Bottle Valve Body
310 Bottle Valve slit
320 Bottle Valve spring bellows
330 Bottle valve seal ring
400 Syringe
500 Barrel
510 Barrel flanges
520 Barrel retaining ring
530 Barrel dose markings
540 Barrel Inner Wall
600 Plunger
604 Plunger rod
610 Plunger Head
620 Plunger Head seal
630 Plunger thumb press
640 Plunger forward stroke stop
650 Plunger dose set grooves
660 Plunger dose markings
700 Valve
710 Valve slit
720 Valve flaps
800 Valve retaining ring
810 Valve retaining ring lugs
900 Dose control clip
910 Clip slot

We claim:

1. A system for dispensing a medication, the system comprising:
the medication wherein the medication is a multiparticulate drug;
a package comprising a bottle to store and dispense the medication,
the bottle comprising a bottom, a bottle wall and a bottle top wall, the bottle top wall further comprising a bottle valve, the bottle valve operable by connection of a dispensing device to the bottle valve;
the bottle valve further comprising a valve body and a dispense nozzle, the valve body having one or more slits therein, and a spring element biasing a slit portion of the valve body to a position distal to an opening of the dispense nozzle;
the dispensing device, the dispensing device being a syringe, comprising:
a barrel for holding the medication, the barrel having an inside, a proximal end and a distal end;
a plunger that is moveable in the inside of the barrel,
the plunger sealing the barrel between the proximal end and a barrel valve;
the plunger further comprising a plurality of dosage setting grooves; a flexible dose control clip, the flexible dose control clip having a tubular construction and a longitudinal separation, the flexible dose control clip configured to fit between two of the plurality of dosage setting grooves;
the barrel valve attached to and closing the distal end of the barrel;
the bottle valve further comprising a guide ring and one or more retaining snaps positioned around the valve body;
the barrel of the syringe further comprising a flexible inwardly protruding ring at or near the proximal end of the barrel of the syringe, the flexible inwardly protruding ring having a diameter that when the flexible dose control clip contacts the flexible inwardly protruding ring, the flexible inwardly protruding ring stops movement of the plunger;
the flexible inwardly protruding ring of the barrel of the syringe or the flexible dose control clip enabling the plunger to be removable from the barrel;
the barrel valve comprising one or more slits therethrough,
the barrel valve further comprising one or more flaps, the one or more flaps joining each other at the one or more slits of the barrel valve, the joined one or more flaps closing the barrel valve, a linear pathway formed within the barrel valve; and
wherein insertion of a distal end of the dispensing device against the bottle valve pushes the valve body of the bottle valve distally to surround the dispense nozzle, compressing the spring element of the bottle valve and forcing the dispense nozzle into the barrel valve, creating a linear pathway within the bottle through which the multiparticulate drug can flow to be dispensed.

2. The system as described in claim 1, wherein withdrawal of the dispensing device from the bottle valve results in closure of the barrel valve and the bottle valve at about a same time.

3. The system as described in claim 1, wherein the dispense nozzle further comprises a plurality of anti-clog ribs, the plurality of anti-clog ribs extending from a proximal end of the dispense nozzle and into the bottle.

4. The system as described in claim 1, wherein the medication is a microsphere.

5. The system as described in claim 1, wherein the medication is a dry powder.

* * * * *